United States Patent
Llosá Llácer et al.

(10) Patent No.: US 11,796,689 B2
(45) Date of Patent: Oct. 24, 2023

(54) DEVICE AND METHOD FOR DETECTING PHOTONS AND CHARGED PARTICLES AND USE OF SAME

(71) Applicants: CONSEJO SUPERIOR DE INVESTIGACIONES CIENTÍFICAS, Madrid (ES); UNIVERSITAT DE VALENCIA, Valencia (ES)

(72) Inventors: Gabriela Dolores Llosá Llácer, Valencia (ES); Carlos Lacasta Llácer, Valencia (ES); John Barrio Toala, Valencia (ES)

(73) Assignees: CONSEJO SUPERIOR DE INVESTIGACIONES CIENTIFICAS, Madrid (ES); UNIVERSITAT DE VALENCIA, Valencia (ES)

( * ) Notice: Subject to any disclaimer, the term of this patent is extended or adjusted under 35 U.S.C. 154(b) by 0 days.

(21) Appl. No.: 17/770,519

(22) PCT Filed: Nov. 4, 2020

(86) PCT No.: PCT/ES2020/070678
§ 371 (c)(1),
(2) Date: Apr. 20, 2022

(87) PCT Pub. No.: WO2021/089899
PCT Pub. Date: May 14, 2021

(65) Prior Publication Data
US 2022/0373698 A1    Nov. 24, 2022

(30) Foreign Application Priority Data
Nov. 7, 2019    (ES) .............. ES201930972

(51) Int. Cl.
*G01T 1/02*     (2006.01)
*A61N 5/10*     (2006.01)
(Continued)

(52) U.S. Cl.
CPC .............. *G01T 1/02* (2013.01); *A61N 5/1071* (2013.01); *G01T 1/2023* (2013.01); *G01T 1/24* (2013.01); *A61N 2005/1087* (2013.01)

(58) Field of Classification Search
CPC ........... G01T 1/02; G01T 1/2023; G01T 1/24; A61N 5/1071
See application file for complete search history.

(56) References Cited

U.S. PATENT DOCUMENTS 9,244,180 B2 * 1/2016 Frisch .................... G01T 1/363
9,535,016 B2   1/2017 Xu
(Continued)

FOREIGN PATENT DOCUMENTS

EP    2293112 A1    9/2011
EP    3056927 A1    8/2016
(Continued)

OTHER PUBLICATIONS

Giacomo Traini, "Design of a new tracking device for on-line beam range monitor in carbon therapy", Journal, 2017, 18-27, vol. 34, Physica Medica.
(Continued)

*Primary Examiner* — Hugh Maupin
(74) *Attorney, Agent, or Firm* — Hayes Soloway PC (57) ABSTRACT

A device for detecting photons and charged particles includes a first photon-detecting panel, which causes a Compton scattering of incident radiation with charged particles, such that the wavelength thereof increases, losing part of their energy, generating a signal. A central charged particle-detecting panel, following the first photon-detecting panel on a side opposite that of the incident radiation, identifies charged particles generated in the first photon-detecting panel, generating a signal. A second photon-detecting panel, follows the central charged particle-detecting panel on a side opposite that of the first photon-detecting panel. Scattered photons and/or charged particles are generated in the first photon-detecting panel interact, generating a signal.

16 Claims, 11 Drawing Sheets

(51) Int. Cl.
*G01T 1/202* (2006.01)
*G01T 1/24* (2006.01)

(56) References Cited

U.S. PATENT DOCUMENTS

| | | | | |
|---|---|---|---|---|
| 2008/0217552 A1* | 9/2008 | Tumer | ............... | A61B 6/4258 |
| | | | | 327/306 |
| 2008/0283764 A1* | 11/2008 | Kerwin | ................ | G01T 1/242 |
| | | | | 250/389 |
| 2014/0110592 A1 | 4/2014 | Nelson et al. | | |
| 2017/0258421 A1* | 9/2017 | Worstell | ............. | A61B 6/032 |
| 2021/0286095 A1* | 9/2021 | Sauli | .................... | G01T 1/023 |

FOREIGN PATENT DOCUMENTS

| | | |
|---|---|---|
| KR | 101866947 B1 | 6/2018 |
| WO | 2011037945 A2 | 3/2011 |
| WO | 2016140371 A1 | 9/2016 |

OTHER PUBLICATIONS

E. Munoz, "Characterization and Simulation Results of a Two-Three-Layer Compton Telescope with LaBr3 and SiPMs", Article, 2015, 1-4, IEEE.

* cited by examiner

DEVICE AND METHOD FOR DETECTING PHOTONS AND CHARGED PARTICLES AND USE OF SAME

CROSS-REFERENCE TO RELATED APPLICATIONS AND PRIORITY

This patent application claims priority from PCT Application No. PCT/ES2020/070678 filed Nov. 4, 2020, which claims priority from Spanish Patent Application No. P201930972 filed Nov. 7, 2019. Each of these patent applications are herein incorporated by reference in their entirety.

OBJECT OF THE INVENTION

The object of the invention falls within the technical field of physics, more specifically within the field of particle detection.

BACKGROUND OF THE INVENTION

One of the main drawbacks of hadron therapy is that there is no effective method to determine in real time whether the radiation dose is being properly applied to the intended site. The detection of secondary particles that escape from the tissue upon being irradiated provides a method for monitoring the therapy. Currently, positron emission tomography is the only method used, but it has serious drawbacks as regards detection efficiency and performance, so alternative monitoring methods are being studied.

One of these alternatives consists of detecting the gamma radiation emitted by the tissue. Currently there are different types of detectors under development for the purpose of detecting the emitted gamma radiation, but they are not in use yet. Both collimated cameras and Compton cameras have been developed.

Collimated cameras are a simple method, close to clinical use, but not very efficient and one that only provides a one-dimensional view of the variations in the application of the dose.

Compton cameras are used or researched for detecting and locating radiation in different fields: astrophysics, national security, locating radioactive sources after nuclear disasters, medical imaging and, recently, in hadron therapy monitoring. In each case they comprise detectors that must be optimised for a specific scenario. Cameras of this type provide a more efficient monitoring method. However, their response is also limited due to the fact that in the clinical application environment a large number of events are detected due to noise, which degrades the signal, an event being considered as an interaction of a charged particle or a photon of the radiation with the detectors or detecting panels.

In Traini, Giacomo et al. *Physica Medica: European Journal of Medical Physics, Volume* 34, 18-27, a device for detecting the origin of secondary charged particles that are produced after the interaction of a carbon ion beam with the tissue of the patient is described, and relates the emission profile of these particles with the position of the Bragg peak and, therefore, with the radiation dose. This device forms part of a larger apparatus that includes a PET (Positron Emission Tomography) detector. The charged particle detector is made up of a series of planes made of scintillator fibres coupled to SiPM (Silicon photomultipliers) and two more scintillators following them.

Document US2014110592 describes a Compton camera for image reconstruction that detects the particles generated in a Compton interaction (gamma radiation and electrons), also describing different modules with different arrangements, and the results are analysed to determine the Compton cone.

Document WO 2016140371 A1 describes a device able to detect the trace (tracking) of energy deposited by an electron emitted in the Compton interaction for better determining the direction of incidence of a gamma ray. The aim of the invention described in this document is to solve the problem of the indeterminacy of the first point of interaction of the gamma ray when multiple scattering occurs in the detector or when another gamma ray interacts simultaneously, and the electron detector is the same in which the first Compton interaction of the photon occurs.

However, tracking entails the use of accurate (and often expensive) detectors, able to detect various electron interactions, and detectors that determine the trace generally have low photon detection efficiency.

In document U.S. Pat. No. 9,535,016 A1, the claimed system comprises a device for improving the efficiency of CT (Computed Tomography) images by using scattered events in the patient. An electron detector that detects the escape of electrons in order to rule out events of this type is proposed in the document.

In the system described in the preceding document, the object to be imaged is located between the source and a gamma radiation-detecting panel. The photons of this invention must be low-energy photons, of the order of those used in CT, since they are intended to interact with the object and be scattered therein.

For the most part, given the low energies of the photons in this document, the electrons emitted in the Compton interaction do not escape from the detecting panel. If they do, they have low energies and are very unlikely to reach the object or the second detector. The problem that arises in this document, and for which adding an electron detector is proposed, is that they take a portion of the energy, which is not deposited in the detector, and thus distort the measurement of the event. Thanks to the electron detector these events can be rejected. The electron detector claims to reject such events, but the electrons do not interact with the object nor with the second detector.

None of the solutions present in the state of the art makes it possible to determine which of the recorded events are good and which are not, in order to discard the latter and improve the signal-to-noise ratio (SNR) without having to reconstruct the trace. They also fail to be easily compatible with structural imaging and reconstruction methods, which would allow a better determination of the irradiated area and of the tumour in therapy applications.

In general, Compton detectors, and in particular those that obtain images using high-energy photons, detect a high number of background events that distort the images obtained. These events are produced both by incident particles on the first detector, different from the photons coming from the object, and by secondary particles generated when the photon interacts with the first detector or with successive detectors.

These particles interact in the different detectors producing random coincidences that the system records as good events, giving rise to noise background in the images. The number of these particles, and therefore of the background events, increases with the energy of the photons.

The proposed invention aims to detect the background events produced by particles generated in the detectors, and additionally charged particles of any type (electrons, positrons, protons, ions, charged fragments), coming from the incident radiation, in order to remove them from the images, something which none of the Compton cameras of the state of the art do. Additionally, it provides information about the event to improve the resolution of the device.

DESCRIPTION OF THE INVENTION

The object of the invention is aimed at improving the signal/noise ratio in a photon-detecting device, by detecting incident charged particles or particles generated by the interaction of photons, and can be used to monitor the radiation dose in hadron therapy.

The detecting device of the first aspect of the invention comprises several detecting planes, interspersing charged particle detectors and photon detectors, preferably from a gamma radiation.

In this way, the detecting device of the first aspect of the invention makes it possible to distinguish between photons and charged particles, reducing the problem of background noise caused by charged particles, thus improving the SNR signal/noise ratio.

Preferably, the detecting device, in a first embodiment, consists of several detecting planes that combine a central charged particle detector (such as a silicon detector, scintillator fibres), with two detectors optimised for detecting (Compton interaction) high-energy photons that are called first photon detector and second photon detector (between hundreds of keV and 10-20 MeV), the central charged particle detector being positioned between both photon detectors and the photons interacting in the photon-detecting panels. The charged particle detector makes it possible to determine whether the signals detected in the second photon detector correspond to the photons scattered in the first photon detector, or to charged particles.

In an alternative embodiment, the device further comprises a frontal charged particle detector, preferably positioned between a source of incident radiation and the first photon-detecting panel, and the central charged particle detector positioned after the first photon-detecting panel, in a side opposite to that of the frontal charged particle-detecting panel. After the central charged particle-detecting panel, the second photon-detecting panel is positioned.

The central charged particle-detecting panel is able to detect charged particles generated by the interaction of photons in the first photon-detecting panel, generating a signal, giving the option both to reject and to take into account this information to reconstruct an event, contributing to more precisely determining the energy deposited in the first photon detector and whether the event is valid or invalid.

The frontal charged particle-detecting panel enables charged particles from incident radiation to be detected and distinguished from photons.

The present invention aims to obtain an image of the photon emission distribution (by means of radiotracer, activation by external irradiation or by being radioactive), such as the body of a patient, and therefore it is the object or patient that acts as a source of radiation and is located in front of the photon-detecting panel or the frontal charged particle-detecting panel, depending on the embodiment.

In the present invention, the photons are not intended to interact with the object, but with the first photon detector. The invention is useful in situations where there are charged particles impinging on the device or where the energy of the photons is sufficient to produce secondary particles, and which can cause increased noise in the image.

Unlike other detectors with a similar application, the device of the alternative embodiment of the invention, which comprises two charged particle-detecting panels and two photon-detecting panels positioned in a sandwich-type structure, enables different types of particles to be distinguished, determining whether the incident particle is a photon (valid event) or a charged particle (valid or invalid event). It also enables determining whether the photons, after interaction in each of the detectors, continue their trajectory or whether the particles produced by the photon in the interaction with the detectors deposit all their energy in the detector, or escape.

This detection ability makes it possible to reconstruct each event and determine which of the recorded events are good and which are not, in order to discard the latter and improve the signal/noise ratio (SNR), and thus the performance of the device of the invention compared to existing or developing systems.

In addition, the device is compatible with structural imaging and reconstruction methods, such as tomography (CAT) and magnetic resonance imaging (MRI), which enables a better determination of the irradiated area and of the tumour.

Therefore, a second aspect of the invention is a method for detecting photons and charged particles.

Likewise, the object of the invention, in a third aspect of the same, is aimed at a use that enables monitoring of the administration of the radiation dose in hadron therapy, preferably based on the gamma radiation photons which are emitted by the tissue when irradiated.

DESCRIPTION OF THE DRAWINGS

To complement the description that is being made and for the purpose of helping to better understand the features of the invention according to a preferred practical exemplary embodiment thereof, a set of drawings is attached as an integral part of said description in which the following is depicted in an illustrative and non-limiting manner.

PREFERRED EMBODIMENT OF THE INVENTION

Figure 1A:
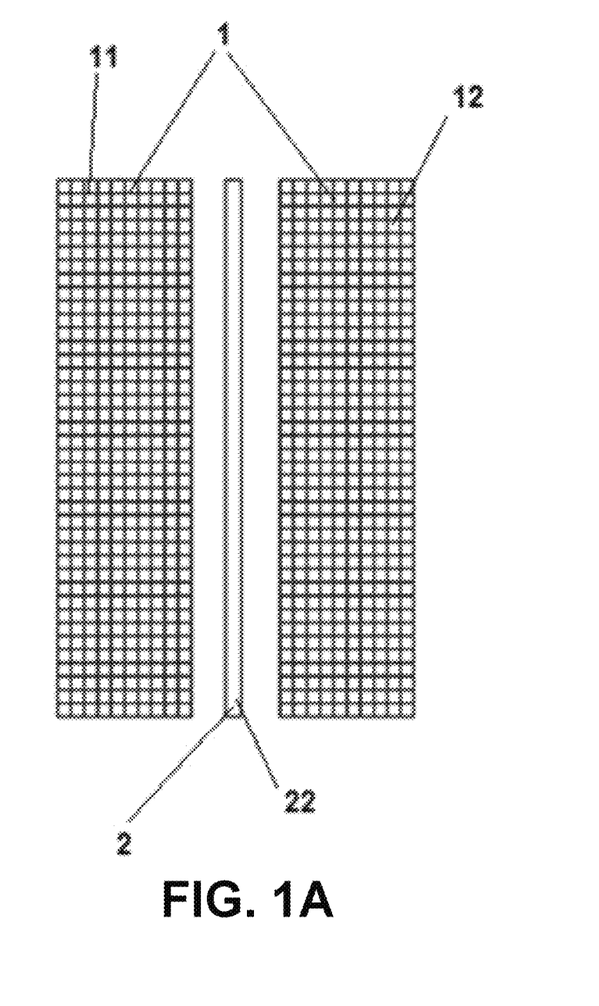
FIGS. 1A and 1B show a schematic view of a first embodiment of the device object of the invention.

In a first preferred embodiment of the device corresponding to a first aspect of the invention, which can be seen in FIG. 1A, there is a device for detecting photons and charged particles, which has a sandwich-type structure, on which a source of radiation impinges, wherein there is, firstly, a first photon-detecting panel (11) that causes a Compton scattering of the incident photons, so that the wavelength thereof increases, losing part of their energy before passing towards a following panel.

After the first photon-detecting panel (11), on a side opposite that of the source of radiation, a central charged particle-detecting panel (22) is located, which detects charged particles generated by the interaction of photons in the first photon-detecting panel (11), generating a signal, giving the option both to reject and to take into account this information to reconstruct an event, contributing to more precisely determining the energy deposited in the first photon-detecting panel (11) and whether the event is valid or invalid. This improves the results of the device.

Finally, in this first embodiment, the device comprises a second photon-detecting panel (12), following the central charged particle-detecting panel (22), on a side opposite that of the incident source of radiation, wherein the photons scattered in the first photon-detecting panel interact. The central charged particle-detecting panel (22) also makes it possible to distinguish whether the particles impinging on the second photon-detecting panel (12) are photons or charged particles.

Figure 1B:
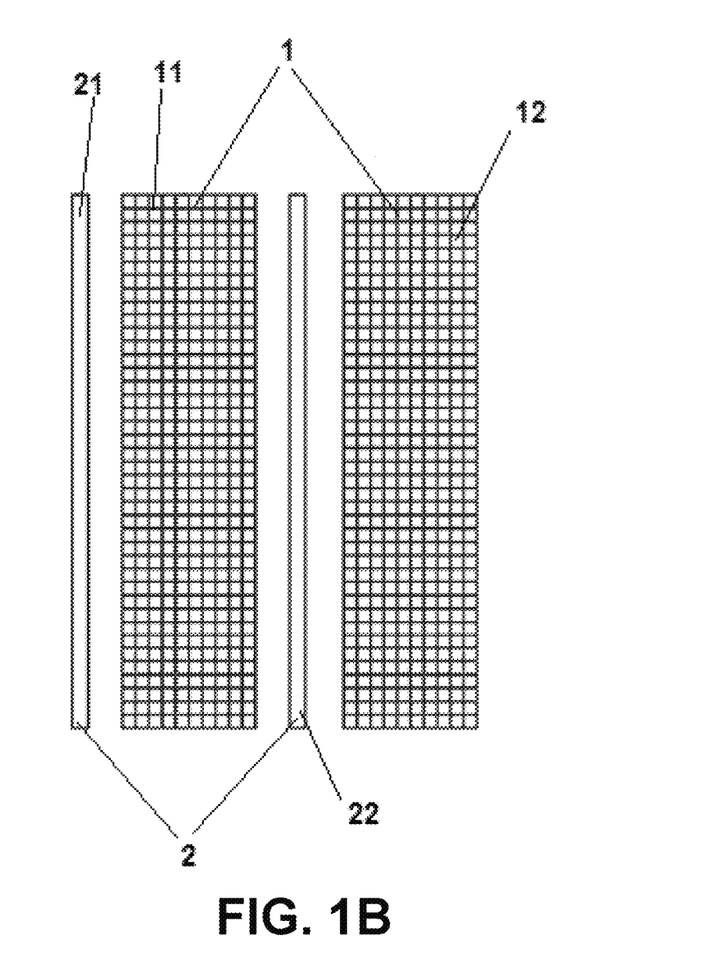

Additionally, in a second embodiment, and as shown in FIG. 1B, the device may comprise a frontal charged particle-detecting panel (21), preferably made of a material comprising Silicon, and located between the incident source of radiation and the first photon-detecting panel (11), which detects charged particles, both from the incident radiation and from the environment, generating a signal when charged particles pass through said frontal detecting panel (21).

Figure 2:
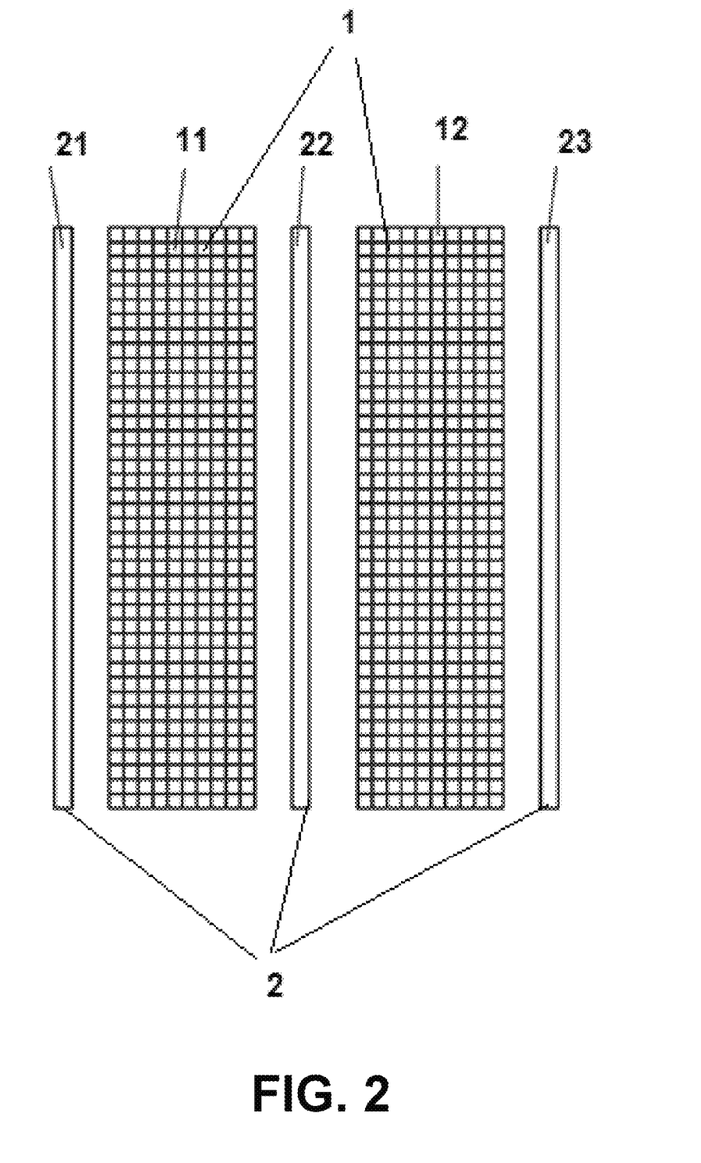
FIG. 2 shows a schematic view of a second embodiment of the device object of the invention.

In a possible third embodiment of the invention, such as the one shown replicated in FIG. 2, the device comprises, in addition to the two photon-detecting panels (11, 12) with scintillator crystals (in this case made of LaBr3, but it can be made of LaBr3, CeBr3, or a CdTe or CZT semiconductor detector), and the frontal charged particle detector (21) and central charged particle detector (22), made up of silicon detectors, a rear charged particle-detecting panel (23), which detects charged particles of the incident radiation that pass through the second photon-detecting panel (12), generating a signal.

In an exemplary embodiment carried out by means of simulation, a ⅜ MeV photon or electron beam is made to impinge and the events that give rise to signals in both photon-detecting panels (11, 12) coinciding in time are recorded, and it is studied whether the Silicon charged particle detectors (21, 22) fulfil their function of helping to distinguish charged particles from photons, i.e., valid events from background noise.

Figure 3:
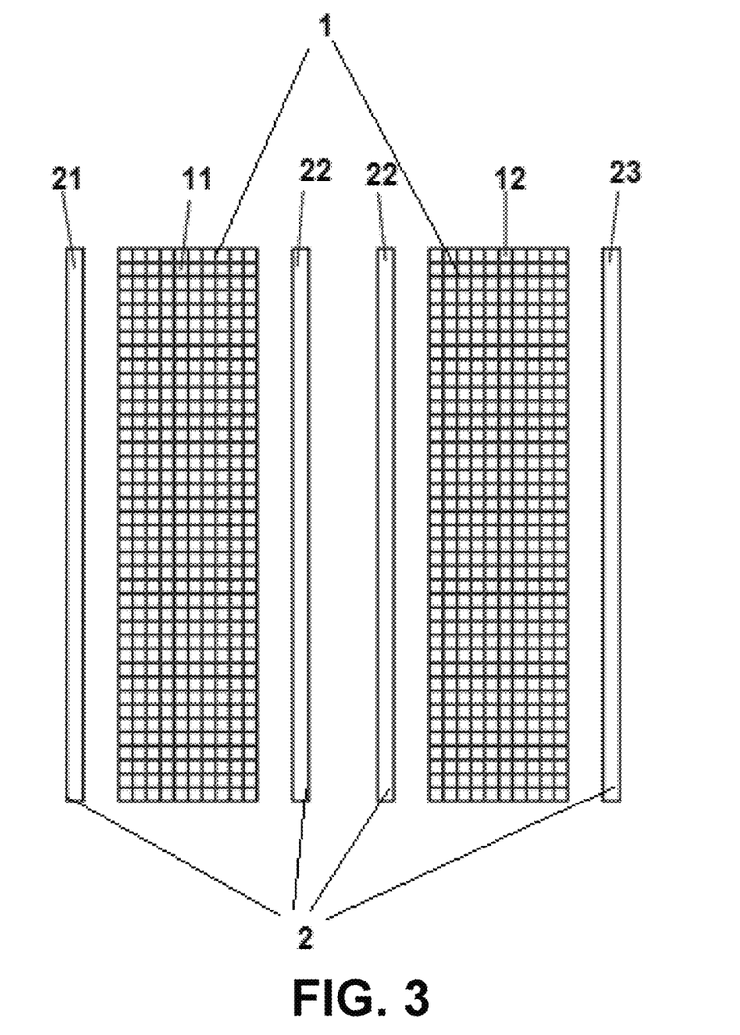
FIG. 3 shows a schematic view of a third embodiment of the device object of the invention.

In a fourth embodiment of the invention shown in FIG. 3, the device further comprises a second central charged particle-detecting panel (22).

In a fifth embodiment of the invention, the device further comprises a third photon-detecting panel (13). Between the three photon-detecting panels (11, 12, 13), a central charged particle-detecting panel (22) and a rear charged particle-detecting panel (23) can be arranged between the second and third photon-detecting panels (22, 23). In addition, a frontal charged particle-detecting panel (21) can be located between the source of radiation and the first photon-detecting panel (11) and/or a rear charged particle-detecting panel (26) can be located after the third photon-detecting panel (13).

Figure 4:
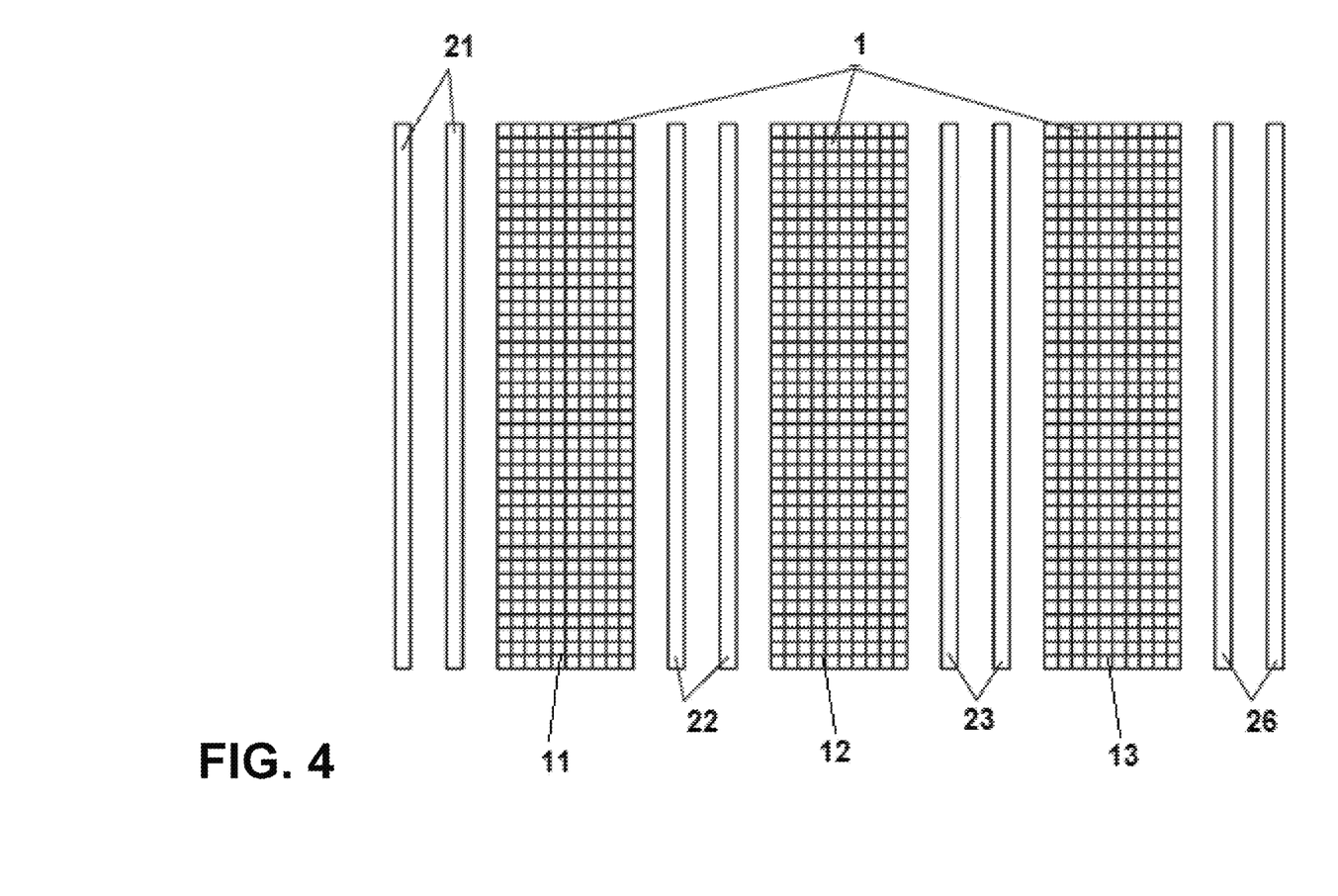
FIG. 4 shows a schematic view of a fourth embodiment of the device object of the invention.

Alternatively, in this fifth embodiment, as shown in FIG. 4, between the source of radiation and the first photon-detecting panel (11), two frontal charged particle-detecting panels (21) and two central charged particle-detecting panels (22) can be located between the first photon detector (11) and the second photon-detecting panel (12). After the latter, two rear charged particle-detecting panels (23) are positioned.

Figure 5:
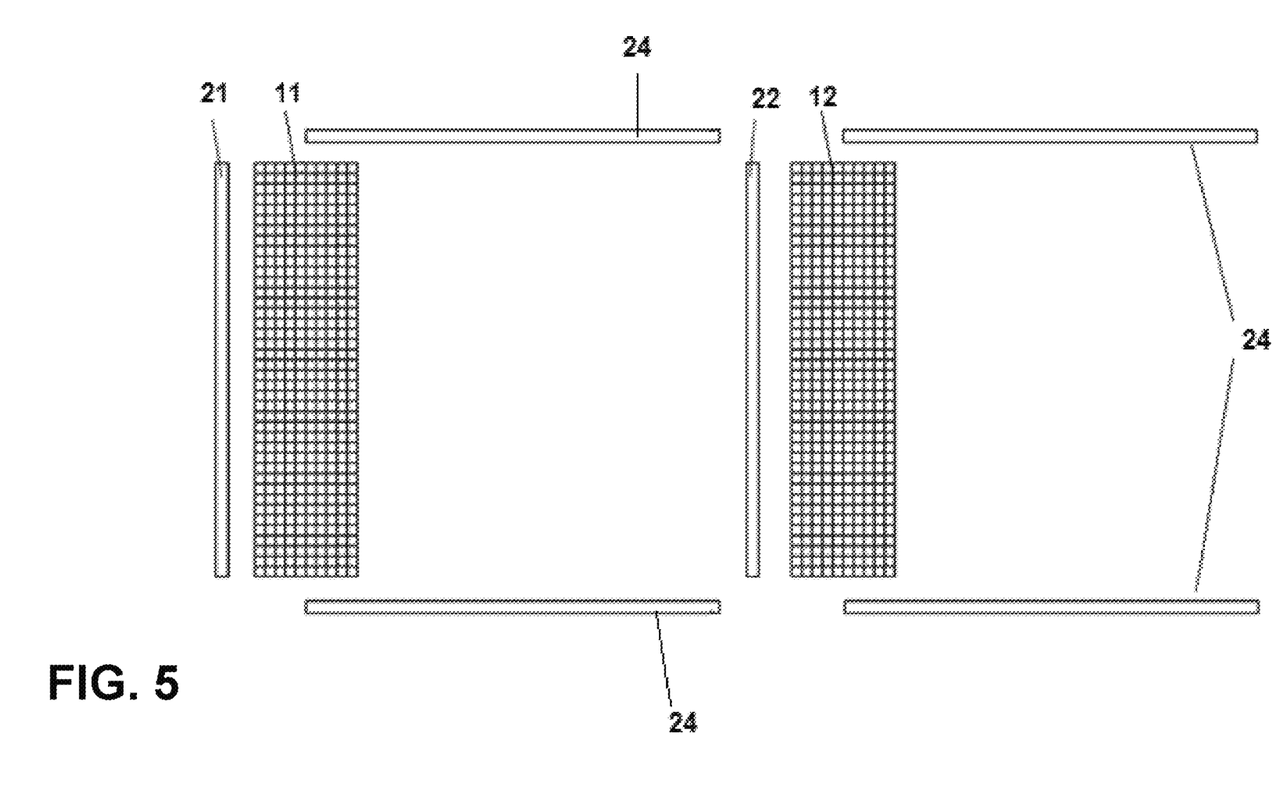
FIG. 5 shows a schematic view of a fifth embodiment of the device object of the invention.

In a sixth alternative embodiment of the invention, shown in FIG. 5, in addition to the elements of the first embodiment described in FIG. 1B, the device comprises two pairs of lateral charged particle detectors (24). Each of the lateral charged particle detectors (24) of each pair is positioned on either side of either the first photon detector (11) or the second photon detector (12), perpendicular thereto. In this way, they are able to detect charged particles of the incident radiation that pass through the photon-detecting panels (11, 12) and that deviate from a perpendicular trajectory thereto.

Figure 6:
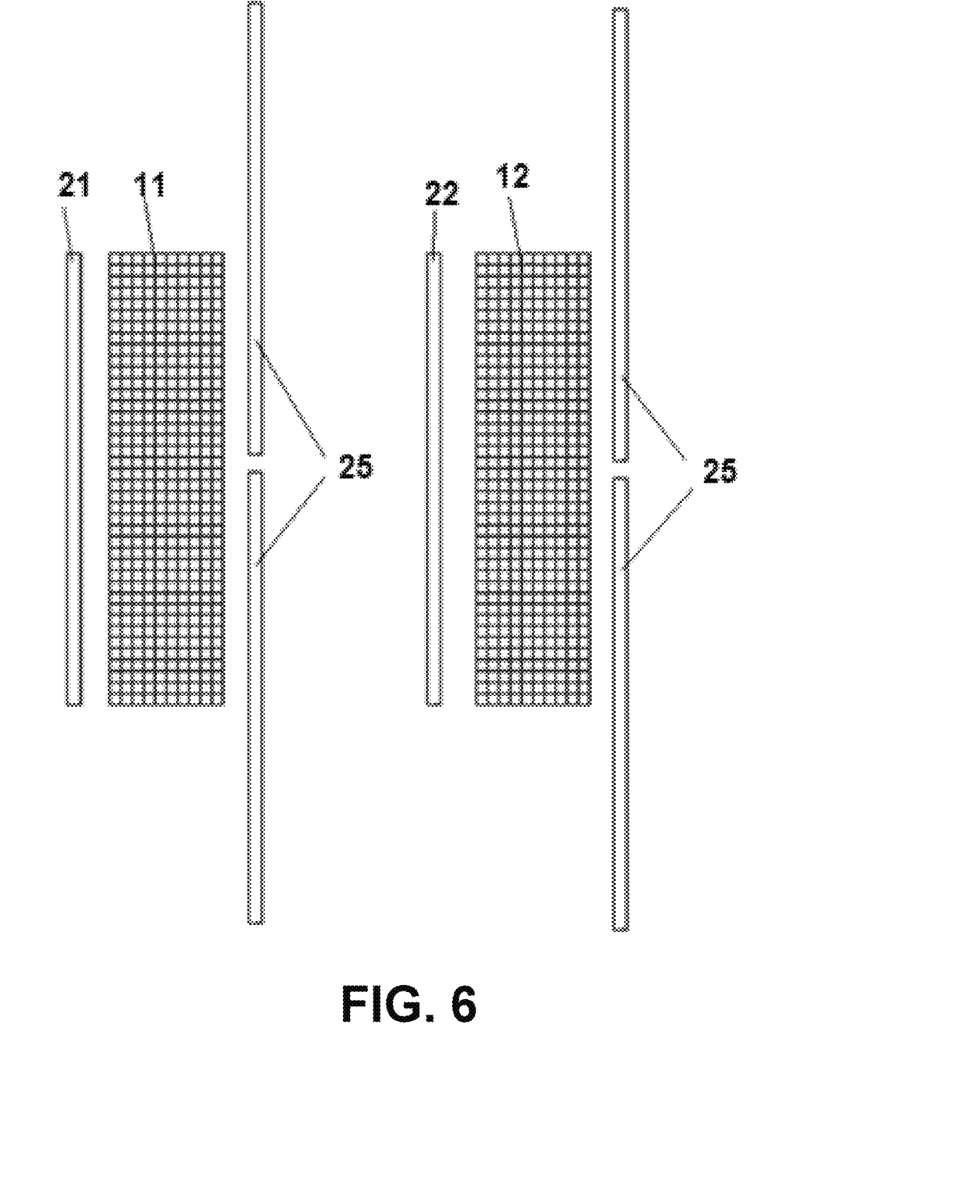
FIG. 6 shows a schematic view of a sixth embodiment of the device object of the invention.

In a seventh embodiment of the invention, reflected in FIG. 6, which comprises all the elements of the first embodiment shown in FIG. 1B, the device additionally comprises two pairs of aligned charged particle detectors (25), the detectors of each pair are positioned one next to the other, and each of the pairs of aligned charged particle detectors (25) are located following the first photon detector (11) and the second photon detector (12). In this way, these detectors are able to detect the charged particles that pass through the photon-detecting panels (11, 12) that deviate from the perpendicular trajectory thereto.

Additionally, and in all the embodiments described above, the device may comprise a first signal detector associated with each photon detector (11, 12, 13) and a second signal detector associated with each charged particle-detecting panel (21, 22, 23, 24, 25, 26).

Two possible cases for implementing the method object of a second aspect of the invention are provided in this document: a first case wherein charged particles reach the device, and a second case wherein gamma radiation impinges on the scintillator crystal of the first photon-detecting panel (11) and the secondary particles generated cause the event to be invalid.

To simulate the first case, a beam of gamma rays or 3 MeV electrons is made to impinge on the device of FIG. 3, which comprises four charged particle-detecting panels (21, 22, 23) between which each of the photon-detecting panels (11, 12) are respectively arranged, on the surface of the frontal charged particle-detecting panel (21), on the left in FIG. 3.

In this case, the photon detectors (11, 12) are made of LaBr3, measure 32×35 mm2 and are 10 mm thick, separated from each other by 30 mm. The events that give rise to signals in both photon detectors (11, 12) coinciding in time are recorded and it is studied whether the charged particle detectors (21, 22, 23) fulfil their function of helping to distinguish valid events from background noise.

When analysing the results, it is observed that 0.715% of the events produce interaction in the two photon-detecting panels (11, 12) in coincidence and therefore are recorded by the device as potentially valid events. However, these events would correspond to noise, since the interaction is not due to photons. Out of them, almost all of the events (0.714%) produce a signal in the frontal charged particle-detecting panel (21), which is located in front of the first photon-detecting panel (11) on the side of incidence of the radiation of the charged particle-detecting panel (11), so they are easily rejected.

In order to illustrate the efficiency of the device in different situations, in the second case various simulations were carried out, with 3 MeV or 6 MeV photon beams that impinge on the device and varying the thickness of the photon detectors (11, 12) between 50 microns and 1000 microns.

Figure 7:
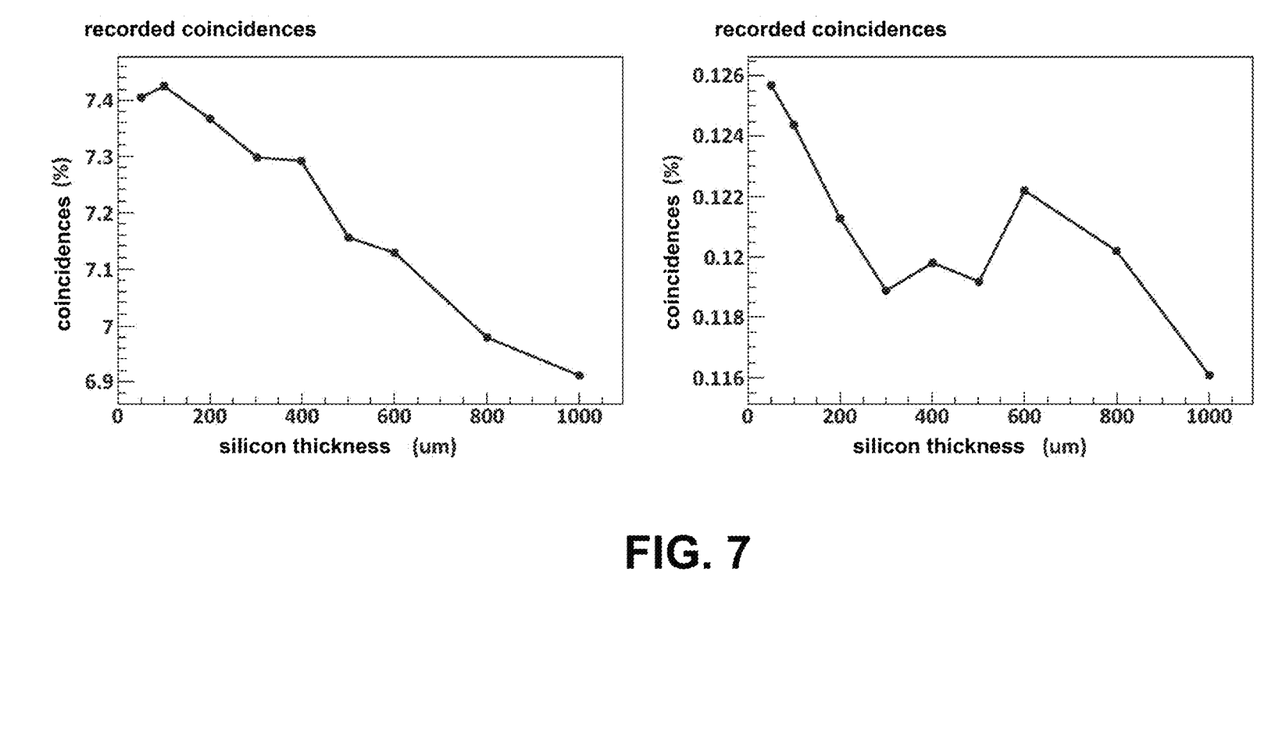
FIG. 7 shows two graphs showing the recorded coincidence values as a function of the thickness of each Si detector of the charged particle detector, for incident 3 MeV (left) and 6 MeV (right) photons.

The percentage of events detected in three cases is studied:

In a first case, referred to in the graphs of FIG. 7, of a total of simulated events (1 million for each thickness of the charged particle-detecting panels (21, 22, 23)), depending on the thickness of the charged particle-detecting panels (21, 22, 23) for incident 3 MeV and 6 MeV photons corresponding to the graph on the left and right, respectively. The recorded values are suitable for two photon-detecting panels (11, 12) in coincidence with the dimensions and geometry studied, and include both good events and bad or noisy events.

Figure 8:
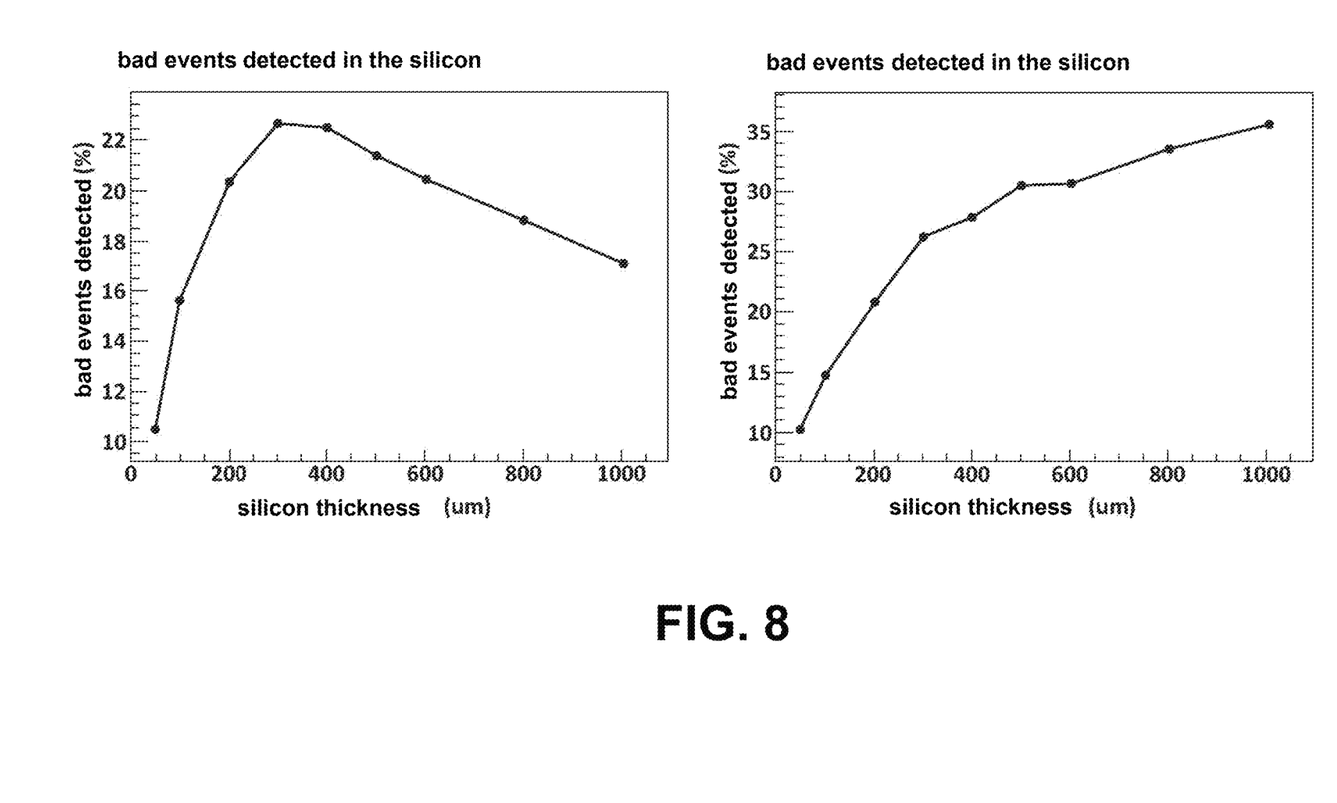
FIG. 8 shows two graphs showing the percentage of noise events that the charged particle detector is capable of detecting for incident 3 MeV (left) and 6 MeV (right) photons.

In a second case, referred to in the graphs of FIG. 8 for incident 3 MeV and 6 MeV radiation photons, in the graph on the left and right, respectively, among the events recorded as coincidences in each case, percentage of noise events that the frontal charged particle-detecting panel (21) is able to detect. These noise events would degrade the response of the first photon detector (21), but due to the frontal charged particle-detecting panel (21) they can be detected and removed from the analysis.

Figure 9:
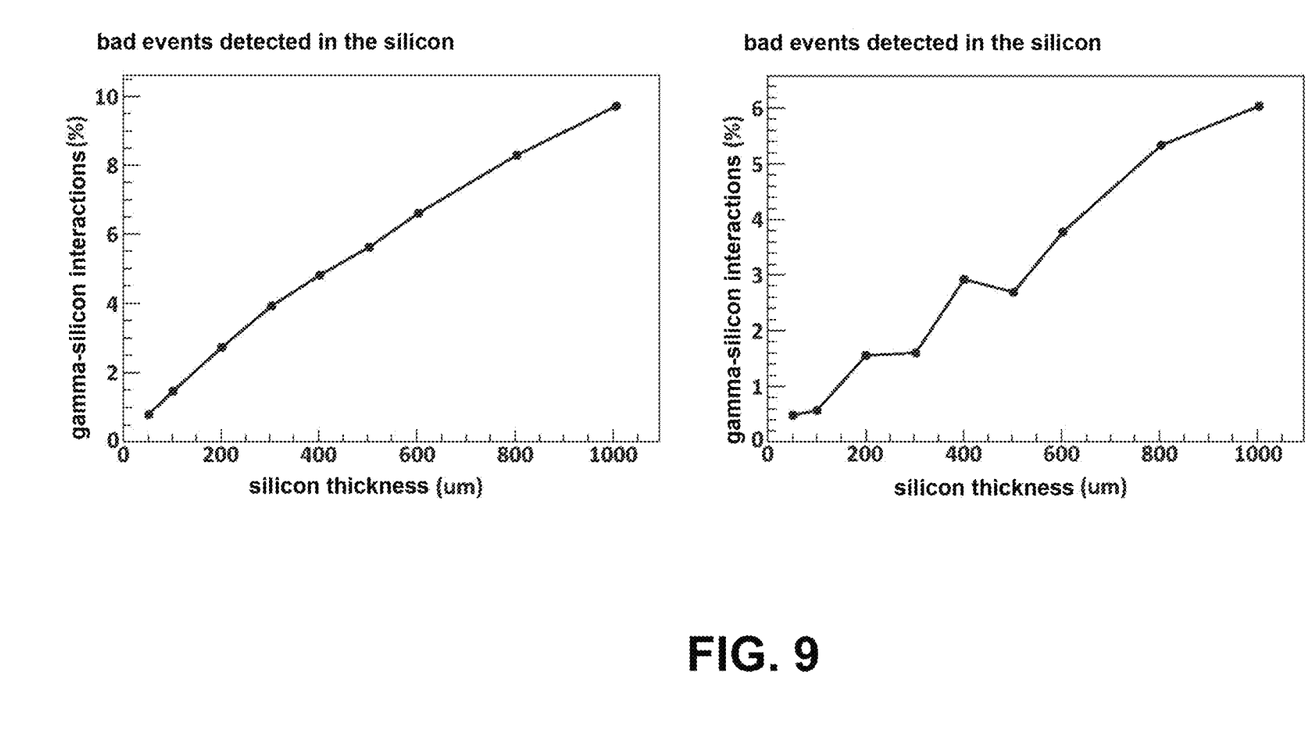
FIG. 9 shows two graphs showing the percentages of primary photons (from the beam) that interact in the silicon for 3 MeV and 6 MeV on the left and right, respectively.

In a third case, referred to in the graphs of FIG. 9, among the events recorded as coincidences in each case, percentage of primary photons (from the incident radiation beam) that interact in the frontal charged particle-detecting panel (21) (for 3 MeV and 6 MeV on the left and right, respectively). These events are unwanted noise events that are generated by including the frontal charged particle-detecting panel (21) in the device.

The object of the invention is able to detect, by means of the frontal charged particle-detecting panel (21), a significant percentage of noise events that would degrade its response (virtually all of the incident charged particles and 20-30% of the recorded coincidences), and can be removed. Noise events generated by introducing the frontal charged particle-detecting panel (21), which in turn can degrade the performance of the device, are kept at low levels. Therefore, performance is improved compared to the devices that incorporate only photon-detecting panels.

Figure 10:
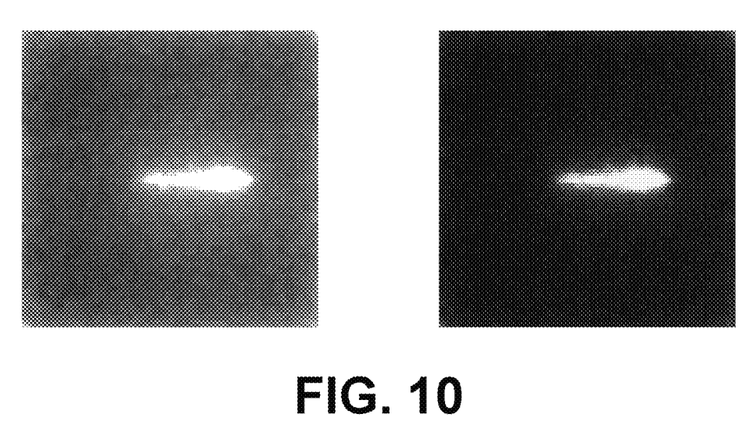
FIG. 10 shows an example of noise reduction in a 2D image of a simulated Bragg peak.

FIG. 10 shows the noise reduction in an image of a simulated Bragg peak. In the image on the left, all events are included. In the image on the right, the events with interaction in Silicon have been removed. As can be seen in FIG. 10, due to the use of the present invention, there is a significant noise reduction in the image.

The images in FIG. 10 have been obtained with a device based on an embodiment like the one in FIG. 3, wherein there is a first photon-detecting panel (11) between two charged particle-detecting panels (21, 22), and a second photon-detecting panel (12) between two other charged particle-detecting panels (22, 23).

The invention claimed is:

1. A device for detecting photons and charged particles, comprising:
   a first photon-detecting panel, which causes a Compton scattering of incident radiation with charged particles, such that the wavelength thereof increases, losing energy in part, generating a signal,
   a central charged particle-detecting panel, following the first photon-detecting panel on a side opposite that of the incident radiation and that identifies charged particles generated in the first photon-detecting panel, generating a signal, and
   a second photon-detecting panel, following the central charged particle-detecting panel, on a side opposite that of the first photon-detecting panel, wherein scattered photons and/or charged particles generated in the first photon-detecting panel interact, generating a signal;
   wherein the central charged particle-detecting panel differentiates photons from charged particles directed to the second photon-detecting panel; and wherein a Compton interaction for detecting high-energy photons is performed between the first photon-detecting panel and the second photon-detecting panel.

2. The device of claim 1, wherein it further comprises a first signal detector associated with each photon detector and a second signal detector associated with each charged particle-detecting panel.

3. The device of claim 1, wherein the photon-detecting panels are detectors based on a scintillator material selected from $LaBr_3$, $CeBr_3$, GAGG or a semiconductor detector selected from CdTe and CZT.

4. A method for detecting photons and charged particles that makes use of the device described in claim 1, wherein it comprises the steps of:
   determining a signal level in at least one of the charged particle-detecting panels by means of signal detector, and
   defining as a negative event when the signal level determined in the preceding step is different from 0.

5. A use of the device described in claim 1 for monitoring radiation doses in hadron therapy.

6. A use of the device described in claim 1 for image reconstruction.

7. A device for detecting photons and charged particles, comprising:
   a first photon-detecting panel, which causes a Compton scattering of incident radiation with charged particles, such that the wavelength thereof increases, losing energy in part, generating a signal;
   a central charged particle-detecting panel, following the first photon-detecting panel on a side opposite that of the incident radiation and that identifies charged particles generated in the first photon-detecting panel, generating a signal;
   a second photon-detecting panel, following the central charged particle-detecting panel, on a side opposite that of the first photon-detecting panel, wherein scattered photons and/or charged particles generated in the first photon-detecting panel interact, generating a signal; and
   a frontal charged particle-detecting panel located between the incident radiation and the first photon-detecting panel, which identifies charged particles from the incident radiation or the environment, generating a signal.

8. The device of claim 7, wherein it further comprises a rear charged particle detector that detects charged particles generated by the interaction of photons in the second photon-detecting panel.

9. The device of claim 8, wherein it further comprises a second central charged particle-detecting panel.

10. The device of claim 9, wherein it further comprises a second frontal charged particle-detecting panel, a second rear charged particle-detecting panel, a third photon-detecting panel following the rear particle-detecting panels, and two rear charged particle-detecting panels, following the third photon-detecting panel.

11. The device of claim 7, wherein it further comprises pairs of lateral charged particle detectors, a first pair being positioned perpendicularly to each side of the first photon detector and a second pair being positioned perpendicularly to each side of the second photon detector.

12. The device of claim 7, wherein it further comprises pairs of aligned charged particle detectors, the aligned charged particle detectors of each pair positioned aligned one next to the other, one of the pairs being positioned between the first photon detector and the central charged particle detector, and a second pair positioned following the second photon detector.

13. A device for detecting photons and charged particles, comprising:
   a first photon-detecting panel, which causes a Compton scattering of incident radiation with charged particles, such that the wavelength thereof increases, losing energy in part, generating a signal;
   a central charged particle-detecting panel, following the first photon-detecting panel on a side opposite that of the incident radiation and that identifies charged particles generated in the first photon-detecting panel, generating a signal;
   a second photon-detecting panel, following the central charged particle-detecting panel, on a side opposite that of the first photon-detecting panel, wherein scattered photons and/or charged particles generated in the first photon-detecting panel interact, generating a signal; and
   a third photon-detecting panel positioned after the second photon-detecting panel, and a rear charged particle-detecting panel positioned between the second photon-detecting panel and the third photon-detecting panel.

14. The device of claim 13, wherein it further comprises a frontal particle-detecting panel positioned between the source of radiation and the first photon-detecting panel.

15. The device of claim 13, wherein it further comprises a rear charged particle-detecting panel positioned after the third photon-detecting panel.

16. The device of claim 13, wherein it further comprises a front particle-detecting panel positioned between the source of radiation and the first photon-detecting panel, and a rear charged particle-detecting panel positioned after the third photon-detecting panel.

\* \* \* \* \*